(12) United States Patent
Uramatsu et al.

(10) Patent No.: US 9,101,617 B2
(45) Date of Patent: Aug. 11, 2015

(54) BASE FOR DRY SOLID DISPERSION, SOLID DISPERSION CONTAINING THE BASE, AND COMPOSITION CONTAINING THE DISPERSION

(75) Inventors: Shunji Uramatsu, Osaka (JP); Akane Kida, Osaka (JP); Hitoshi Shinike, Osaka (JP); Toshinobu Uemura, Kishiwada (JP); Yoshinobu Fukumori, Kakogawa (JP)

(73) Assignees: Daido Chemical Corporation, Osaka-Shi (JP); Nisshin Kasei Co., Ltd., Osaka-Shi (JP)

( * ) Notice: Subject to any disclaimer, the term of this patent is extended or adjusted under 35 U.S.C. 154(b) by 615 days.

(21) Appl. No.: 12/450,967

(22) PCT Filed: Apr. 15, 2008

(86) PCT No.: PCT/JP2008/057322
§ 371 (c)(1),
(2), (4) Date: Oct. 20, 2009

(87) PCT Pub. No.: WO2008/133102
PCT Pub. Date: Nov. 6, 2008

(65) Prior Publication Data
US 2010/0120924 A1    May 13, 2010

(30) Foreign Application Priority Data

Apr. 20, 2007  (JP) .................................. 2007-111937

(51) Int. Cl.
*A61K 31/4422* (2006.01)
*A61K 9/14* (2006.01)
*A61K 9/20* (2006.01)

(52) U.S. Cl.
CPC ............. *A61K 31/4422* (2013.01); *A61K 9/146* (2013.01); *A61K 9/2027* (2013.01); *A61K 9/2095* (2013.01)

(58) Field of Classification Search
None
See application file for complete search history.

(56) References Cited

U.S. PATENT DOCUMENTS

| | | | |
|---|---|---|---|
| 4,990,335 A | | 2/1991 | Bateman et al. |
| 5,340,591 A | * | 8/1994 | Nakano et al. ................. 424/499 |
| 2003/0170309 A1 | * | 9/2003 | Babcock et al. ............... 424/486 |
| 2004/0156905 A1 | | 8/2004 | Babcock et al. |
| 2006/0229383 A1 | * | 10/2006 | Noami et al. ................. 523/160 |

FOREIGN PATENT DOCUMENTS

| | | |
|---|---|---|
| CN | 1681479 A | 10/2005 |
| EP | 1 530 457 A1 | 5/2005 |
| EP | 1657265 A1 | 5/2006 |
| JP | 05-262642 A | 10/1993 |
| JP | 2004-534811 | 11/2004 |
| JP | 2006-500349 | 1/2006 |

OTHER PUBLICATIONS

First Office Action for Chinese Patent Application No. 200880012243.X dated Jan. 19, 2011.
G. Kiyonaka et al., "Application of Ultrasound Compacting to Solid Dispersion," Journal of Pharmaceutical Science and Technology, vol. 60, No. 2, 2000, pp. 148-159.
International Search Report mailed Jul. 22, 2008, issued on PCT/JP2008/057322.
Christian Leuner et al., "Improving drug solubility for oral delivery using solid dispersions," European Journal of Pharmaceutics and Biopharmaceutics, vol. 50, 2000, pp. 47-60.
Supplementary European Search Report dated Aug. 10, 2010, issued for the European Patent Application No. 08740408.3.
H. Suzuki et al. "Influence of Water-Soluble Polymers on the Dissolution of Nifedipine Solid Dispersions with Combined Carriers," Chem. Pharm. Bull 46(3), 482-487 (1998).

* cited by examiner

*Primary Examiner* — Michael B Pallay
(74) *Attorney, Agent, or Firm* — Locke Lord LLP; James E. Armstrong, IV; Nicholas J. DiCeglie, Jr.

(57) ABSTRACT

The present invention provides a novel base material for a dry solid dispersion, a solid dispersion containing the base material, and a composition containing the dispersion; the solid dispersion of the present invention, which contains a poorly soluble component with improved dissolvability, can be obtained by mixing a polyvinyl alcohol-based copolymer, as a base material for the dry solid dispersion, with a poorly soluble component, and then heating it.

7 Claims, 4 Drawing Sheets

BASE FOR DRY SOLID DISPERSION, SOLID DISPERSION CONTAINING THE BASE, AND COMPOSITION CONTAINING THE DISPERSION

TECHNICAL FIELD

The present invention relates to a technique by which a poorly soluble component can be made into a solid dispersion. More specifically, the present invention relates to a technique to obtain a solid dispersion by adding a polyvinyl alcohol-based copolymer (preferably, polyvinyl alcohol/acrylic acid/methylmethacrylate copolymer) as a base for solid dispersion to a poorly soluble component, followed by heating with ultrasonic waves, heat transmission, etc.

BACKGROUND ART

In recent years, solid dispersions have attracted attention in the field of oral preparations. Generally, solid dispersions can be obtained by suitably selecting one or more components to be added to a poorly soluble medicament, the production method, etc. Solid dispersions are expected to improve the dissolvability of the poorly soluble medicament so as to enhance its bioavailability.

One example of a well-known method for producing solid dispersions is the solvent method. The solvent method is such that, for example, both the polymer material that is used as a base for solid dispersion and the medicament are dissolved in an organic solvent, and then dried to make the poorly soluble medicament amorphous so that it can be dispersed on a polymer carrier. However, the solvent method adversely affects the environment due to the organic solvent used. For this reason, a dry process has attracted attention as a method which does not require an organic solvent.

One typical example of a method for producing a solid dispersion employing the dry method is that heating and melting a poorly soluble medicament and a base for solid dispersion (carrier) so as to make the medicament amorphous (the hot melt extruder method). Another example of a known method is placing a mixture of a poorly soluble medicament and a base for solid dispersion in a mortar for molding, followed by irradiation with ultrasonic waves to make the medicament amorphous (for example, Non-Patent Document 1), etc.

The former method is a direct heating method, wherein the mixture of a poorly soluble medicament and a base for solid dispersion carrier is directly heated. On the other hand, the latter method is an indirect heating method, wherein the energy generated by irradiation with ultrasonic waves triggers movement and friction in the powder. As a result, the mixture stores heat and is accordingly made amorphous.

Still another example of a known method to produce a solid dispersion is a thermal mechanochemical method, wherein a poorly soluble medicament (nilvadipine, nifedipine) and a water-soluble polymer base (hydroxypropylmethyl cellulose, polyvinyl pyrrolidone) are mixed while being heated at a temperature at which neither of them are melted (for example, Patent Document 1).

Examples of conventionally known bases for solid dispersion usable in such dry methods include polyvinyl pyrrolidone (PVP), hydroxypropylmethyl cellulose (HPMC), hydroxypropylmethyl cellulose phthalate (HPMCP), polyvinyl alcohol (PVA), etc. However, a base for solid dispersion that is more desirable for use in a dry method has been demanded in view of the temperature during the heat treatment, degree of the improvement in the dissolvability of a poorly soluble medicament, stability and reproducibility of the dissolvability of poorly soluble medicament, etc.

Patent Document 1: Japanese Unexamined Patent Publication No. 1993-262642
Non-patent Document 1: Journal of Pharmaceutical Science and Technology, Vol. 60 (No. 2), 148-159 (2000)

DISCLOSURE OF THE INVENTION

Problem to be Solved by the Invention

An object of the present invention is to provide a solid dispersion by which the dissolvability of poorly soluble components, including poorly soluble medicaments, is improved.

Means for Solving the Problem

The present inventors conducted extensive research in order to solve the above problem and found that a solid dispersion having an excellent ability in dissolving poorly soluble components can be obtained by using a polyvinyl alcohol-based copolymer as a base for solid dispersion and mixing and heating it with a poorly soluble component. The present invention has been accomplished based on this finding.

Specifically, the present invention provides bases for solid dispersion, solid dispersions, medical compositions, and production methods as described below.

Item 1. A base for solid dispersion consisting of a polyvinyl alcohol-based copolymer.

Item 2. The base for solid dispersion according to Item 1, wherein the polyvinyl alcohol-based copolymer is obtained by copolymerizing at least one member selected from the group consisting of polyvinyl alcohols and derivatives thereof with at least one member selected from the group consisting of polymerizable vinyl monomers.

Item 3. The base for solid dispersion according to Item 1, wherein the polymerizable vinyl monomer comprises at least an acrylic acid monomer and a methylmethacrylate monomer.

Item 4. The base for solid dispersion according to Item 3, wherein the contents of acrylic acid monomer and methylmethacrylate monomer relative to the total weight of at least one member selected from the group consisting of polyvinyl alcohols and derivatives thereof and at least one member selected from the group consisting of polymerizable vinyl monomers are respectively 0.5 to 20 weight % and 5 to 40 weight %.

Item 5. The base for solid dispersion according to Item 1, wherein the polyvinyl alcohol-based copolymer is a copolymer in which an acrylic acid and a methylmethacrylate are graft polymerized to the polyvinyl alcohol chain.

Item 6. The base for solid dispersion according to Item 5, wherein the contents of acrylic acid monomer residue and methylmethacrylate monomer residue that compose the polyvinyl alcohol-based copolymer are respectively 0.5 to 20 weight % and 5 to 40 weight % relative to the polyvinyl alcohol-based copolymer.

Item 7. The base for solid dispersion according to any one of Items 1 to 6, wherein the weight average molecular weight of the polyvinyl alcohol-based copolymer is 10,000 to 500,000.

Item 8. A solid dispersion comprising a poorly soluble component and polyvinyl alcohol-based copolymer.

Item 9. The solid dispersion according to Item 8, which is formed by heating a mixture of a poorly soluble component and a polyvinyl alcohol-based copolymer.

Item 10. The solid dispersion according to Item 9, wherein the heating is conducted by one means selected from supersonic treatment, biaxial kneading treatment, melting treatment, uniaxial and biaxial melt-extruding treatment, microwave treatment, and thermal mechanochemical treatment, or a combination thereof.

Item 11. The solid dispersion according to any one of Items 8 to 10, wherein the weight of the polyvinyl alcohol-based copolymer is 0.5 to 20 times the weight of the poorly soluble component.

Item 12. A medical composition comprising the solid dispersion defined in any one of Items 8 to 11.

Item 13. A method for producing a solid dispersion comprising the step of:
heating a mixture of a poorly soluble component and a base for solid dispersion,
the base for solid dispersion being that defined in any one of Items 1 to 7.

The base for solid dispersion of the present invention is a polyvinyl alcohol-based copolymer that is used together with a poorly soluble component in the production of a solid dispersion. The poorly soluble component becomes amorphous when heated with the base for solid dispersion of the present invention, the dissolvability of the poorly soluble component thereby being improved.

The solid dispersion of the present invention comprises a poorly soluble component and a heated article of the base for solid dispersion of the present invention, wherein the poorly soluble component exhibits a high solvability. In the solid dispersion of the present invention, a part or whole of the poorly soluble component is amorphous. Taking advantage of its excellent dissolvability, the solid dispersion of the present invention may be added to medicines, agricultural chemicals, fertilizers, cosmetics, flavors, food materials, fodder, germicides, antibacterial agents, repellents, insecticides, antirust agents, absorbents, coating compositions, etc. The existence of the solid dispersion can be confirmed by observing the melting peaks in a differential scan calorimetric analysis (DSC).

The medical composition of the present invention contains the solid dispersion of the present invention, has an increased dissolvability of a poorly soluble component (medicament), and exhibits improved bioavailability.

The method for producing the solid dispersion of the present invention is as explained below. A mixture containing a poorly soluble component, the base for solid dispersion of the present invention, and optionally one or more additives is heated to make the poorly soluble component amorphous, obtaining a solid dispersion having improved dissolvability of poorly soluble component.

The present invention is explained in detail below.

The poorly soluble component used in the present invention can be selected from various compounds such as pharmaceutical compounds (including animal drugs), agricultural-chemical compounds, fertilizers, cosmetics, flavors, food materials, fodders, germicides, antibacterial agents, repellents, insecticides, antirust agents, absorbents, coating compositions, etc.

When in a crystalline condition, the poorly soluble component used in the present invention is poorly soluble in water. Therefore, a part or whole of the poorly soluble component is contained in the solid dispersion of the present invention in an amorphous state. The term poorly soluble means the solubility in water at 25° C. is less than 10 mg/mL, and preferably less than 0.1 mg/mL. The solubility can be measured in a standard method.

The poorly soluble components include poorly soluble medicaments. Specific examples of the poorly soluble medicaments are shown below.

(1) Antipyretic Agents, Analgesic Agents, and Antiinflammatory Agents:

Examples of antipyretic agents, analgesic agents and anti-inflammatory agents include salicylic acid, sulpyrine, flufenamic acid, dichlofenac, indomethacin, atropine, scopolamine, morphine, pethidine, levorphanol, ketoprofen, naproxen, ibuprofen, oxymorphone, aspirin, aminopyrine, phenacetin, acetaminophen, phenylbutazon, ketophenylbutazone, mefenamic acid, bucolome, benzydamine, mepirizole, tialamide, tinoridine, Xylocaine, pentazocine, dexamethasone, hydrocortisone, prednisolone, azulene, isopropylantipyrine, sasapyrine, clofezone, Etodolac, and salts thereof.

(2) Tranquilizers:

Examples of tranquilizers include diazepam, lorazepam, oxazepam, oxazolam, clotiazepam, medazepam, temazepam, fludiazepam, meprobamate, nitrazepam, chlordiazepoxide, etc.

(3) Antipsychotic Agents:

Examples of antipsychotic agents include chlorpromazine, prochlorperazine, trifluoperazine, sulpiride, clocapramine hydrochloride, zotepine, haloperidol, etc.

(4) Antibacterial Agents:

Examples of antibacterial agents include griseofulvin, lankacidins [J. Antibiotics, 38, 877-885 (1985)], azole-based compounds, such as 2-[(1R,2R)-2-(2,4-difluorophenyl)-2-hydroxy-1-methyl-3-(1H-1,2,4-triazole-1-yl)propyl]-4-[4-(2,2,3,3-tetrafluoropropoxy)phenyl-3-(2H,4H)-1,2,4-triazolone, fluconazole, itraconazole, etc.; nalidixic acid, piromidic acid, pipemidic acid trihydrate, enoxacin, cinoxacin, ofloxacin, norfloxacin, ciprofloxacin hydrochloride, sulfamethoxazole-trimethoprim, etc.

(5) Antibiotics:

Examples of antibiotics include gentamycin, dibekacin, Kanendomycin, Lividomycin, tobramycin, amikacin, dibekacin, fradiomycin, sisomycin, tetracycline, oxytetracycline, rolitetracycline, doxycycline, ampicillin, piperacilin, ticarcillin, cephalotin, cefotiam, cefotiam hexetil, cefsulodin, cefmenoxime, cefmetazole, cefazolin, cefotaxime, cefoperazone, ceftizoxime, moxalactam, thienamycin, sulfazecin, azthreonam, amoxicillin, cephalexin, erythromycin, bacampicillin, minocycline, chloramphenicol and salts thereof.

(6) Antineoplastic Agents:

Examples of antineoplastic agents include 6-O—(N-chloroacetyl carbamoyl) fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, Picibanil, lentinan, levamisole, bestatin, azimexon, glycyrrhizin, HER2 inhibitor (heterocyclic compounds and the like disclosed in WO01/77107, etc.), taxol, doxorubicin hydrochloride, etoposide, mitoxantrone, mesna, dimesna, aminoglutethimide, tomoxifen, acrolein, cisplatin, carboplatin, cyclophosphamide, lomustine (CCNU), carmustine (BCNU), etc.

(7) Hypolipidemic Drugs:

Examples of hypolipidemic drugs include clofibrate, 2-chloro-3-[4-(2-methyl-2-phenylpropoxy)phenyl]ethyl propionate [Chem. Pharm. Bull., 38, 2792-2796 (1990)], clinofibrate, cholestyramine, soysterol, tocopherol nicotinate, nicomol, niceritrol, probucol, elastase, etc.

(8) Antitussive and Expectorants:

Examples of antitussive and expectorants include ephedrine, methylephedrine, noscapine, codeine, dihydrocodeine, alloclamide, chlorfedianol, picoperidamine, cloperastine, protokylol, isoproterenol, salbutamol, thalline, bromhexine, carbocysteine, ethylcysteine, methylcysteine and salts thereof.

(9) Muscle Relaxants:

Examples of muscle relaxants include pridinol, tubocurarine, pancuronium, chlorphenesin carbamate, tolperisone hydrochloride, eperisone hydrochloride, tizanidine hydrochloride, mephenesin, chlorzoxazone, phenprobamate, methocarbamol, chlormezanone, pridinol mesilate, afloqualone, baclofen, dantrolene sodium, etc.

(10) Antiepileptic Agents:

Examples of antiepileptic agents include phenytoin, ethosuximide, acetazolamide, chlordiazepoxide, phenobarbital, carbamazepine, primidone, etc.

(11) Antiulcer Agents:

Examples of antiulcer agents include lansoprazole, metoclopramide, famotidine, omeprazole, sulpiride, trepibutone, cetraxate hydrochloride, gefarnate, irsogladine maleate, cimetidine, ranitidine hydrochloride, nizatidine, roxatidine acetate hydrochloride, etc.

(12) Antidepressants:

Examples of antidepressants include imipramine, clomipramine, noxiptiline, phenelzine, etc.

(13) Antiallergic Drugs:

Examples of antiallergic drugs include diphenhydramine, chlorpheniramine, tripelenamine, methodiramine, clemizole, diphenylpyraline, methoxyphenamine, clemastine fumarate, cyproheptadine hydrochloride, mequitazine, alimemazine tartrate, etc.

(14) Cardiotonic Drugs:

Examples of cardiotonic drugs include trans-pi-oxocamphor, terenol, aminophylline, etilefrine, etc.

(15) Antiarrhythmic Agents:

Examples of antiarrhythmic agents include propranolol, alprenolol, bufetolol, oxprenolol, procainamide hydrochloride, disopyramide, ajmaline, quinidine sulfate, aprindine hydrochloride, propafenone hydrochloride, mexiletine hydrochloride, etc.

(16) Vasodilator Drugs:

Examples of vasodilator drugs include oxyfedrine, diltiazem, tolazoline, hexobendine, bamethan, nifedipine, nilvadipine, isosorbit dinitrate, diltiazem hydrochloride, trapidil, dipyridamole, dilazep hydrochloride, verapamil, nicardipine hydrochloride, ifenprodil tartrate, cinepazide maleate, cyclandelate, cinnarizine, pentoxifylline, etc.

(17) Antihypertensive and Diuretic Agents:

Examples of antihypertensive and diuretic agents include hexamethonium bromide, pentolinium, mecamylamine, ecarazine, clonidine, diltiazem, nifedipine, furosemide, trichlormethiazide, methyclothiazide, hydrochlorothiazide, hydroflumethiazide, ethiazide, cyclopenthiazide, florothiazide, ethacrynic acid, etc.

(18) Antidiabetic Agents:

Examples of antidiabetic agents include glymidine, glipizide, phenformin, buformin, metformin, glibenclamide, tolbutamide, etc.

(19) Antitubercular Agents:

Examples of antitubercular agents include isoniazid, ethambutol, para-aminosalicylic acid, etc.

(20) Antinarcotics:

Examples of antinarcotics include levallorphan, nalorphine, naloxone and salts thereof.

(21) Hormonal Drugs:

Examples of hormonal drugs include steroid hormones, such as dexamethasone, hexestrol, methimazole, betamethasone, triamcinolone, triamcinolone acetonide, fluocinolone acetonide, prednisolone, hydrocortisone, estriol, etc.

(22) Osteochondropathy Prevention and Treating Agents:

Examples of osteochondropathy prevention and treating agents include prostaglandin A1 derivative, vitamin D derivatives, vitamin K2 derivatives, eicosapentaenoic acid derivatives, benzylphosphonate, bisphosphonic acid derivatives, sex-hormone derivatives, phenolsulfophthalein derivatives, benzothiopyran or benzothiepine derivatives, thienoindazole derivatives, menatetrenone derivatives, helioxanthin derivatives and like non-peptidic osteogenesis-promotion enhancers; peptidic osteogenesis-promotion enhancers; etc.

(23) Articular Disorder Treating Agents:

Examples of articular disorder treating agents include p38MAP kinase inhibitors (e.g., thiazole-based compounds and the like disclosed in WO 00/64894, etc.), matrix-metalloprotease inhibitors (MMPI), prednisolone, hydrocortisone, methylprednisolone, dexa/betamethasone, betamethasone and like anti-inflammatory steroid drugs; indomethacin, diclofenac, loxoprofen, ibuprofen, piroxicam, sulindac and like non-steroidal anti-inflammatory drugs; etc.

(24) Hydrochlorides for Use in Treating Pollakiuria:

Examples of hydrochlorides for use in treating pollakiuria include flavoxate, oxybutynin hydrochloride, terodiline hydrochloride, etc.

(25) Antiandrogenic Agents:

Examples of antiandrogenic agents include oxendolone, allylestrenol, chlormadinone acetate, gestonorone caproate, osaterone acetate, flutamide, bicalutamide, etc.

(26) Fat-Soluble Vitamin Agents:

Examples of fat-soluble vitamin agents include vitamins $K_1$, $K_2$, $K_3$, $K_4$ and like vitamins K: folic acid (vitamin M), etc.

(27) Vitamin Derivatives:

Examples of vitamin derivatives include 5,6-trance-cholecalciferol, 2,5-hydroxycholecalciferol, 1-α-hydroxycholecalciferol and like vitamin $D_3$ derivatives; 5,6-trance-ergocalciferol and like vitamin $D_2$ derivatives; etc.

(28) Others:

Examples of other poorly soluble medicaments include hydroxycam, diacerein, megestrol acetate, nicergoline, prostaglandins, anti-ischemic agents, anti-immunopathy agents, Alzheimer's disease therapeutic agents, antiosteoporotic agents, angiogenesis agents, antiretinopathy agents, retinal-vein-occlusion therapeutic agents, senile-disciform-macular-degeneration therapeutic agents, cerebral-vasospasm therapeutic agents, anti-thrombotic agents, cerebral infarction therapeutic agents, brain-obstruction therapeutic agents, intracerebral-hemorrhage therapeutic agents, subarachnoid-hemorrhage therapeutic agents, hypertensive-encephalopathy therapeutic agents, transient-ischemic-attack therapeutic agents, multiinfarct dementia therapeutic agents, anti-arteriosclerosis agents, anti-Huntington disease agents, brain tissue damage therapeutic agents, optic neuropathy therapeutic agents, anti-glaucoma agents, anti-ocular hypertension agents, retinodialysis therapeutic agents, antiarthritic agents, antirheumatic agents, antisepsis agents, septic-shock prevention agents, antiasthmatic agents, atopic dermatitis therapeutic agents, allergic rhinitis therapeutic agents, etc.

From the viewpoint of improving dissolvability, preferable examples of poorly soluble medicaments include indomethacin, naproxen, ibuprofen, phenacetin, phenylbutazon, griseofulvin, azole-based compounds, phenytoin, sosorbit dinitrate, nitrophenylpyridine-based compounds (nifedipine, nilvadipine, etc.). The nitrophenylpyridine-based compounds include poorly soluble compounds having a nitrophenyl group and a pyridine ring structure. Preferable examples of the nitrophenylpyridine-based compounds include compounds having a nitrophenyl group bonded at the 2- or 4-position of a pyridine ring. Specific examples of such compounds include nifedipine, nilvadipine, etc.

Examples of poorly soluble agricultural-chemicals are as shown below.

(1) Insecticides:
(a) Carbamate Insecticides:
Examples of carbamate insecticides include MIPC (isoprocarb), BPMC (fenobucarb), MPMC (xylylcarb), XMC, NAC (carbaryl), bendiocarb, carbofuran, etc.
(b) Synthetic Pyrethroid-Based Insecticides:
Examples of synthetic pyrethroid-based insecticides include cypermethrin, fenpropathrin, ethofenprox, resmethrin, etc.
(c) Organic Phosphorus-Based Insecticides:
Examples of organic phosphorus-based insecticides include EPN, cyanofenphos, PAP (phenthoate), CVMP (tetrachlorvinphos), monocrotophos, phosalone, chlorpyrifos-methyl, chlorpyrifos, pyridaphenthion, quinalphos, DMTP (methidathion), dioxabenzofos, etc.
(d) Organic Hydrochloride-Based Insecticides:
Examples of organic hydrochloride-based insecticides include endosulfan, etc.
(e) Others:
Examples other insecticides include bensultap, buprofezin, flufenoxuron, diflubenzuron, chlorfluazuron, imidacloprid, etc.
(2) Germicides:
(a) N-heterocycle-Based Ergosterol Inhibitors:
Examples of N-heterocycle-based ergosterol inhibitors include triflumizole, triforine, etc.
(b) Carboxyamide-Based Germicides:
Examples of carboxyamide-based germicides include mepronil, flutoluanil, pencycuron, oxycarboxin, etc.
(c) Dicarboxyimide-Based Germicides:
Examples of dicarboxyimide-based germicides include iprodione, vinclozolin, procymidone, etc.
(d) Benzimidazole-Based Germicides:
An example of dicarboxyimide-based germicide is benomyl.
(e) Polyhaloalkylthio-Based Germicides:
An example of polyhaloalkylthio-based germicide is captan.
(f) Organic Hydrochloride-Based Germicides:
Examples of organic hydrochloride-based germicides include fthalide, TPN chlorothalonil, etc.
(g) Sulfur-Based Germicides:
Examples of sulfur-based germicides include zineb, maneb, etc.
(h) Others:
Examples of other germicides include diclomezin, tricyclazole, isoprothiolane, probenazole, anilazine, oxolinic acid, ferimzone, etc.
(3) Herbicides:
(a) Sulfonylurea-Based Herbicides:
Examples of sulfonylurea-based herbicides include imazosulfuron, bensulfuron-methyl, etc.
(b) Triazine-Based Herbicides:
Examples of triazine-based herbicides include simetryn, dimethametryn, etc.
(c) Urea-Based Herbicides:
An example of urea-based herbicides is dymron.
(d) Acid Amide-Based Herbicides:
Examples of acid amide-based herbicides include propanil, mefenacet, etc.
(e) Carbamate-Based Herbicides:
An example of carbamate-based herbicide is swep.
(f) Diazole-Based Herbicides:
Examples of diazole-based herbicides include oxadiazon, pyrazolate, etc.
(g) Dinitroaniline-Based Herbicides:
An example of dinitroaniline-based herbicide is trifluralin.
(h) Others:
An example of other herbicide is dithiopyr.

In a solid dispersion, a polymer carrier (polymer compound, surfactant, etc.) is usually used as a base for solid dispersion that is used together with a poorly soluble component. However, in the present invention, a polyvinyl alcohol-based copolymer is used as the base for the solid dispersion. By heating a mixture of this copolymer and a poorly soluble component, a part or whole of the poorly soluble component becomes amorphous, obtaining a solid dispersion containing a poorly soluble component with improved dissolvability. The form of the poorly soluble component in the mixture is usually a powder, and the polyvinyl alcohol-based copolymer is also usually a powder, having an average particle diameter of preferably 0.1 to 2000 μm and more preferably 0.1 to 500 μm. Mixing these components can be conducted by selecting an appropriate method, for example, by using a V-shaped mixer, a rotary vessel-type mixer, a mixer with blades, etc.

The weight of the polyvinyl alcohol-based copolymer used in the present invention is generally 0.5 to 20 times, preferably 1 to 10 times, and more preferably 2 to 10 times that of the poorly soluble component. The mass average molecular weight of the polyvinyl alcohol-based copolymer is generally 10,000 to 500,000, and preferably 35,000 to 300,000.

The polyvinyl alcohol-based copolymer may be produced by a known method. An example of the method is disclosed in WO02/17848, wherein a polyvinyl alcohol and a polymerizable vinyl monomer are polymerized in the presence of at least one member selected from the group consisting of polyvinyl alcohols and derivatives thereof. Examples of the derivatives of polyvinyl alcohols include amine-modified polyvinyl alcohols, ethylene-modified polyvinyl alcohols, and polyvinyl alcohols with a modified terminal thiol group, etc.

The content of each component for use in forming the polyvinyl alcohol-based copolymer per the total weight of the at least one member selected from the group consisting of polyvinyl alcohols and derivatives thereof and the polymerizable vinyl monomers is as below. The content of the at least one member selected from the group consisting of polyvinyl alcohols and derivatives thereof is generally 40 to 95 weight % and preferably 60 to 90 weight %. The content of the polymerizable vinyl monomer is generally 5 to 60 weight % and preferably 10 to 40 weight %.

Examples of the polymerizable vinyl monomers are as shown below and these polymerizable vinyl monomers may be used singly or in combination.

(1) Acrylic acid, methacrylic acid, fumaric acid, maleic acid, itaconic acid;

(2) sodium salts, potassium salts, ammonium salts, and alkylamine salts of the compounds listed in (1); and (3) methylmethacrylate, methylacrylate, ethylmethacrylate, ethylacrylate, butylmethacrylate, butylacrylate, isobutylmethacrylate, isobutylacrylate, cyclohexylmethacrylate, cyclohexylacrylate, 2-ethylhexyl methacrylate, 2-ethylhexylacrylate, laurylmethacrylate, laurylacrylate, stearylmethacrylate, stearylacrylate, acrylonitrile, acrylamide, dimethylacrylamide, styrene, vinyl acetate, hydroxyethylmethacrylate, hydroxyethylacrylate, esters of polyethylene glycol and methacrylic acid, esters of polyethylene glycol and acrylic acid, esters of polypropylene glycol and methacrylic acid, esters of polypropylene glycol and acrylic acid, N-vinylpyrrolidone, acryloylmorpholine, N,N-dimethylaminoethylmethacrylate, methacrylatoethyl trimethyl ammonium chloride.

A preferable polymerizable vinyl monomer is a compound shown in General Formula [1] below.

$$H_2C=C(R^1)-COOR^2 \qquad [1],$$

wherein $R^1$ represents a hydrogen atom or a methyl group, $R^2$ represents a hydrogen atom or a $C_{1-4}$ alkyl group.

Preferable combinations of polymerizable vinyl monomers involve a use of at least one monomer of (1) and (2) together with at least one monomer of (3). More preferable combinations of polymerizable vinyl monomers involve a combined use of methylmethacrylate with acrylic acid or methacrylic acid, i.e., a combination of acrylic acid with methylmethacrylate and a combination of methacrylic acid with methylmethacrylate. A further preferable combination is acrylic acid with methylmethacrylate. A particularly preferable polyvinyl alcohol-based copolymer can be obtained by polymerizing 0.5 to 20 weight % of acrylic acid, 5 to 40 weight % of methylmethacrylate, and 40 to 94.5 weight % of polyvinyl alcohol per total weight of the acrylic acid, methylmethacrylate and polyvinyl alcohol. A still more preferable polyvinyl alcohol-based copolymer can be obtained by polymerizing 2.5 to 5.0 weight % of acrylic acid, 15 to 25 weight % of methylmethacrylate, 20 to 70 weight % of polyvinyl alcohol. The copolymer obtained by polymerizing acrylic acid and methylmethacrylate in the presence of a polyvinyl alcohol is commercially available ("Povacoat" manufactured by Daido Chemical Corporation). In the present invention, "Povacoat" may be used.

Copolymerization may be conducted by a known method. The resin can be produced by, for example, adding at least one member selected from the group consisting of polyvinyl alcohols and derivatives thereof to water; dissolving it by heating; adding at least one polymerizable vinyl monomer and a polymerization initiator thereto; followed by polymerization or copolymerization. The polymerization initiator is optionally used, and may be a conventionally used one. Examples of polymerization initiators include 2,2'-azobis(2-amidinopropane)dihydrochloride, AIBN (azobisisobutyronitrile) and like azo compounds; potassium persulfate, sodium persulfate, ammonium persulfate and like persulfates; t-butyl hydroperoxide and like organic peroxides; hydrogen peroxide/tartaric acid, hydrogen peroxide/sodium tartrate and like redox initiators; etc.

When the solid dispersion of the present invention is used in a form of medical composition, the medical composition may contain any components commonly used as raw materials for a preparation, as long as they will not adversely affect the effects of the present invention, various pharmaceutically acceptable carriers, excipients, lubricants, binders, disintegrators, surfactants, preservatives, antioxidants, coloring agents, sweetening agents and the like. These carriers may be used singly or in combination. Other medicinal properties may be added if necessary. The medical composition can be prepared by suitably employing a known preparation method. The medical composition may be prepared, for example, by adding an additive to the solid dispersion and then forming the medical composition into a desirable formulation. A solid dispersion obtained by simply heating a poorly soluble medicament, the base for solid dispersion of the present invention and additives without modification may also be usable as a medical composition. It is also possible to add an additive to the thus-obtained solid dispersion and formulate it into a medical composition.

Examples of the additives are listed below:

Excipients, such as sugar alcohols (maltitol, xylitol, sorbitol, erythritol, etc.), lactose, saccharose, sucrose, sodium chloride, glucose, starch, sucrose, mannitol, reduced palatinose, carbonates (calcium carbonate, etc.), kaolin, crystalline cellulose, silicic acid, methylcellulose, sodium alginate, gum arabic, talc, phosphates (potassium hydrogenphosphate, calcium hydrogenphosphate, sodium dihydrogenphosphate, dipotassium phosphorate, potassium dihydrogenphosphate, calcium dihydrogenphosphate, sodium dihydrogenphosphate), calcium sulfate, calcium lactate, and oligosaccharides (lactulose, raffinose, lactosucrose, etc.);

Plasticizers, such as glycerol, ethylene glycol, propylene glycol and like polyhydric alcohols; monostearins, PEG4000, PEG6000, PEG20000 and like waxes; stearic acid, magnesium stearate and like organic fatty acids;

Surfactants, such as triethyl citrate, Tween 80, HCO60, and triacetin;

Viscosity modifiers, such as simple syrup, glucose liquid, starch liquid, and gelatin solution;

Binders, such as hydroxypropyl cellulose, polyvinyl alcohol, polyvinyl ether, polyvinyl pyrrolidone, hydroxypropylmethyl cellulose, hydroxyethyl cellulose, carboxyvinyl polymer, crystalline cellulose, powder cellulose, crystalline cellulose-carmellose sodium, shellac, methylcellulose, ethylcellulose, potassium phosphate, powder gum arabic, pullulan, pectin, dextrin, corn starch, pregelatinized starch, hydroxypropyl starch, gelatin, xanthan gum, carrageenan, tragacanth, powdered tragacanth, and polyethylene glycol;

Disintegrators, such as starch, dry starch, sodium carboxymethyl cellulose, calcium carboxymethyl cellulose, croscarmellose sodium, sodium carboxymethyl starch, methyl cellulose, carmellose calcium, low substituted hydroxypropylcellulose, sodium carboxymethyl starch, partially pregelatinized starch, sodium alginate, powdered agar, sodium bicarbonate, and calcium carbonate;

Absorbefacients, such as quarternary ammonium salt, and laurylsodium sulfate;

Adsorbents, such as starch, lactose, kaolin, bentonite, and colloid silicic acid;

Lubricants, such as magnesium stearate, calcium stearate, talc, magnesium oxide, colloidal silica, powdered boric acid, and polyethylene glycol;

Dispersants, such as sucrose fatty acid esters, sorbitan fatty acid esters, and saponin;

Antioxidants, such as ascorbic acid and tocopherol;

Acidulants, such as lactic acid, citric acid, gluconic acid, and glutamic acid;

Plasticizers, such as silicon dioxide;

Sweeteners, such as a sucralose, acesulfame potassium, aspartame, and glycyrrhizin; and Flavoring agents, such as mentha oil, eucalyptus oil, cinnamon oil, fennel oil, clove oil, orange oil, lemon oil, rose oil, fruit flavor, mint flavor, peppermint powder, dl-menthol, and l-menthol.

In order to easily control the dissolution rate of the poorly soluble medicament, it is preferable that a disintegrator, binder and the like are added. In order to make the heating temperature during the production of a solid dispersion as low as possible, it is preferable that a plasticizer and the like be added (in particular, when a melting method is employed). In extrusion or injection molding, it is preferable that a plasticizer, lubricant and the like be added to reduce the extrusion resistance. In order to reduce the static electricity generated during the production process, it is desirable to blend antistats, such as talc and silica.

The solid dispersion of the present invention can be desirably used as a medicinal composition for oral administration without modification. If necessary, additives may be added to the solid dispersion of the present invention, and formed into subtle granules, fine granules, granules, tablets, capsules, suppositories, ointments, plasters, cataplasms, aerosols and the like. Among these, tablets, subtle granules, fine granules, granules, and capsules are preferable.

The content of the solid dispersion of the present invention in the medical composition is generally 0.1 to 100 weight %. The dose of the medical composition containing the solid dispersion of the present invention can be suitably selected depending on the content and bioavailability of the medicinal properties.

The solid dispersion of the present invention can be produced by heating a mixture of a poorly soluble component and the base for solid dispersion of the present invention, i.e., a polyvinyl alcohol-based copolymer, and then desirably formulating (grinding, pulverizing, molding, etc.) the heated mixture if necessary.

The mixture of the poorly soluble component and the polyvinyl alcohol-based copolymer may be heated at a temperature wherein all the components of the mixture are melted, or a temperature wherein some components are melted. Alternatively, the temperature may be selected so that some or all of the poorly soluble components become amorphous, if not melted, according to the properties of the components. The average particle diameters and the proportions of the poorly soluble component and the polyvinyl alcohol-based copolymer in the mixture are as described above.

There is no limitation to the heating means in the heating treatment, and any heating means available to a person having ordinary skill in the art may be suitably employed. Specific examples thereof include heating by an oven, oil bath, electric furnace or the like; heating by ultrasonic irradiation; heating by a biaxial kneading treatment; heating by a uniaxial or biaxial melt-extruding treatment (extruder); heating by microwave irradiation; etc.

There is no limitation to the means for formulating the heat treated mixture and the means may be suitably selected from those available to a person having ordinary skill in the art. Specific examples thereof include grinding, molding, etc. Specific examples of the molding means include extrusion molding (uniaxial extrusion, biaxial extrusion, multiaxial extrusion, hot melt calender method), injection molding (for example, biaxial extrusion), compression molding (for example, tableting, granulating), etc.

When production of the solid dispersion by heating and formulation of the solid dispersion are simultaneously conducted, it is desirable to employ a method provided with a heating means for formulating a heat-treated material.

The temperature for the heat treatment does not necessarily have to be at which the heated substance will be melted. It is known that a solid dispersion can be obtained at a temperature lower than the melting temperature. Using this feature, in the present invention, a poorly soluble component that decomposes or deteriorates at a high temperature can be made into a solid dispersion by preparing a solid dispersion at a temperature as low as possible. The heating temperature is generally 130 to 200° C., preferably 140 to 190° C., and more preferably 150 to 180° C. Ultrasonic irradiation is conducted by irradiating the powder mixture with ultrasonic waves. When heating is conducted by ultrasonic irradiation, the ultrasonic irradiation energy is generally 600 to 2000 J, preferably 700 to 1800 J, and more preferably 800 to 1300 J. One example of the device for conducting such ultrasonic irradiation is the ultrasonic tableting machine USTM/L20 manufactured by Tecnea Engineering Srl. This device is for conducting compression molding after placing a powder mixture of a poorly soluble component, a base material for solid dispersion, and optional additives in a mortar of the device, and then irradiating the mixture with ultrasonic waves.

There are several biaxial extrusion molding machines, biaxial extruders and the like provided with a heating means. Examples of the preferable heating treatments in the present invention include those conducted using a means for conducting compression molding while irradiating ultrasonic waves, a biaxial extrusion molding machine provided with a heating means, and a biaxial extruder provided with a heating means.

Effects of the Invention

The present invention provides a solid dispersion containing a poorly soluble component with an improved dissolvability, a base usable for the solid dispersion, and a medical composition containing the solid dispersion.

BRIEF DESCRIPTION OF THE DRAWINGS

FIG. 3 is a chart of differential scanning calorimetry (DSC) measured in Test Example 3 (DSC measured using a product treated with supersonic with NIF/POVA=1/5). In FIG. 3, NIF represents nifedipine and POVA represents POVACOAT Type F.

BEST MODE FOR CARRYING OUT THE INVENTION

Hereunder, the present invention is explained in detail below with reference to Examples, Comparative Examples and Test Examples. However, the scope of the present invention is not limited to these.

EXAMPLES

In the Examples and Comparative Examples explained below, production, experiment, measurement, etc., were conducted with the materials, devices, methods, conditions and procedures as explained below.

1. Materials:

POVACOAT Type F; Polyvinyl alcohol-based copolymer (copolymer obtained by polymerizing acrylic acid, methylmethacrylate and polyvinyl alcohol) manufactured by Daido Chemical Corporation Nifedipine (NIF); Ground product
Polyvinyl alcohol (PVA)
Polyvinyl pyrrolidone (PVP)

2. Ultrasonic Molding Conditions:
 Device: Ultrasonic tableting machine; USTM-L20 (manufactured by Tecnea Engineering Srl.)
 Device conditions:
  Diameter of mortar; 25 mm
  Air pressure; 0.4 MPa
  Irradiation calorie; 670 J to 1200 J
 Procedures:
  1. NIF (nifedipine) and the base for solid dispersion were weighed in a manner such that they have a specific compounding ratio, and manually mixing them to form a homogeneous powder mixture.
  2. One gram of the powder mixture is weighed and placed in a mortar.
  3. The exposure amount is set and the device is then operated.
3. DSC Measurement Conditions:
 Device: DSC6220 (manufactured by SII NanoTechnology Inc.)
 Device conditions:
  Programming rate; 10° C./minute
  Measurement range; 30 to 220° C.
  Carrier gas; nitrogen, 40 mL/minute
  Pan; Open
4. Elution Test Measurement Conditions:
  The Japanese Pharmacopoeia, Method 2 (paddle method)
  Stirring rate; 50 rpm
  Test liquid; purified water, 900 mL
  Measurement temperature; 37±0.5° C.
  Amount of sample; in an amount equivalent to NIF content of 90 mg
  Measuring time; 0 to 180 minutes
5. Melt Indexer Elution Test Measurement Conditions:
 Device: Melt Indexer P101 (manufactured by Toyo Seiki Seisaku-Sho, Ltd.)
 Device conditions:
  Diameter of injection cylinder; 9 mm
  Diameter of orifice; 2 mm
  Amount of sample; Powder mixture of 3 g
 Procedures:
  1. Heat the cylinder (diameter of 9 mm) in the device to a predetermined temperature.
  2. The sample powder is placed in a cylinder that was heated to a predetermined temperature, and then pressed from the upper direction using a piston provided in the upper part of the cylinder.
  3. The sample powder is melted and extruded from the orifice (diameter of 2 mm) provided in the bottom portion of the cylinder.

Examples 1 to 3

Ultrasonic Molding of Poorly Soluble Nifedipine Preparation Using Polyvinyl Alcohol-Based Polymer In the ultrasonic molding of the below-mentioned Examples and Comparative Examples, a USTM/L-20 ultrasonic tableting machine manufactured by Tecnea Engineering Srl. was employed. The tableting machine is provided with a discoid shaped mortar with a center portion (25.0 mm in diameter) passing therethrough from top to bottom, lower and upper pestles having a shape matched to that of the center portion, and an ultrasonic wave oscillating device mounted on the upper portion of the upper pestle to allow the center portion being irradiated with ultrasonic waves through the upper pestle. Molding was performed by setting the lower pestle onto the lower portion of the center portion of the mortar, introducing the preparation material into the cavity between the mortar and the lower pestle, and then pushing the lower pestle upwardly via air pressure while ultrasonic waves from the ultrasonic wave oscillating device being applied onto the preparation material through the upper pestle.

Nifedipine is an antihypertensive agent, which is a yellow crystalline powder, with the physical properties of a melting temperature of 172° C. to 175° C., and a water solubility of 7 µg/ml to 8 µg/ml (poorly soluble). It was confirmed by measurement via differential scanning calorimeter (DSC) that a crystalline nifedipine had a melting peak in the vicinity of 174° C. The nifedipine was prepared by adding a polyvinyl alcohol-based powder as the base for solid dispersion and employing an ultrasonic tableting machine.

POVACOAT Type F (manufactured by Daido Chemical Industry, Co.; average molecular weight of about 40,000; average particle size of 125 µm; hereinafter, referred to as "POVA") was used as the base for solid dispersion.

A mixture was prepared by mixing nifedipine with the base for solid dispersion in an amount five times the weight of the nifedipine. One gram of the mixture was used as the preparation material and formed into a 25 mm in diameter tablet (thickness of about 1 mm) by use of the ultrasonic tableting machine. The nifedipine content per 1 g tablet was 167 mg.

The push-up pressure of the lower pestle was set at 0.4 MPa, and the irradiation energy of the ultrasonic waves was set at 670 J (Example 1), 1000 J (Example 2), and 1200 J (Example 3).

Comparative Example 1

Ultrasonic Molding of Lactose and Nifedipine Mixture

The ultrasonic molding was conducted in the same manner as in Example 2 except that lactose was used as the base for solid dispersion in an equal weight to that of nifedipine. The amount of ultrasonic irradiation energy was 1000 J. However, due to the extreme fragility thereof, the product obtained by ultrasonic irradiation was an unformed powder.

Comparative Example 2

Ultrasonic Molding of Nifedipine Preparation Using PVA

The nifedipine preparations were prepared by conducting ultrasonic molding in the same manner as in Example 2 except that polyvinyl alcohol (PVA) was used as the base for solid dispersion. The amount of ultrasonic irradiation energy was 1000 J.

Comparative Example 3

Ultrasonic Molding of Nifedipine Preparation Using PVP

The nifedipine preparations were prepared by conducting ultrasonic molding in the same manner as in Example 2 except that polyvinyl pyrrolidone (PVP) was used as the base for solid dispersion. The amount of ultrasonic irradiation energy was 1000 J.

Experimental Example 1

Elution Test 1 of Nifedipine (Active Ingredient) in Water

Figure 1:
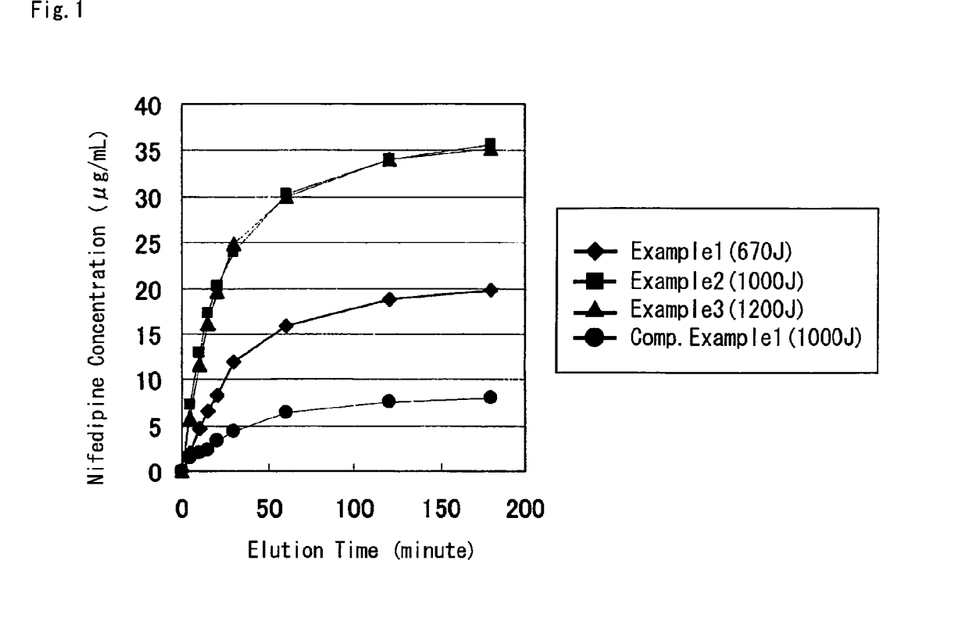
FIG. 1 is a graph showing the nifedipine concentration (μg/mL) (vertical axis) and the elution time (minute) (horizontal axis) in Test Example 1.

The tablets formed in Example 1 to 3 were pulverized using a coffee mill, the obtained pulverized product was used as the test sample, and the elutability in water of the active ingredient, i.e., nifedipine, was tested. The powder obtained in Comparative Example 1 was used as a test sample without modification, and the elutability of nifedipine was tested in the same manner. The elution test was conducted in accordance with an "elution test method" in the general test methods defined by the Japanese Pharmacopoeia. The elution test is conducted to measure the elution of the principal constituents from a solid preparation. The experimental method of the present invention is briefly explained below. The first method of the elution test (rotary basket method) was employed. An amount of a powder obtained in Comparative Example 1 and the tablets formed in Examples 1 to 3 equivalents to a nifedipine content of 90 mg were used as the test samples, and 900 ml of distilled water was added to each test sample. Each test solution was extracted at predetermined times (0, 5, 10, 15, 20, 30, 60, 120, and 180 min), filtered through a 0.45 µm filter, the filtrate was passed through a spectrophotometer, the absorbance was measured at 235 nm, and the nifedipine concentration (µg/ml) was then calculated. The results are shown in FIG. 1.

When 180 minutes passed from the initiation of the test, the test sample of Example 1 exhibited a nifedipine elutability about 2.5 times that of the test sample of Comparative Example 1. The test samples of Examples 2 and 3 exhibited nifedipine elutabilities about 4.4 times to 4.5 times that of the test sample of Comparative Example 1. Therefore, the test samples of Examples 1 to 3 had superior bioavailability in terms of the active ingredient elutability. The elution performance of the test sample of Comparative Example 1 was the almost the same level as that (i.e., 7 µg/ml to 8 µg/ml) of a mixture in which lactose and nifedipine were physically compounded at a weight ratio of 1:1 (a mixture to which additional treatments causing chemical reactions, such as heating, are not applied).

Experimental Example 2

Elution Test 2 of Active Ingredient (Nifedipine) in Water

Figure 2:
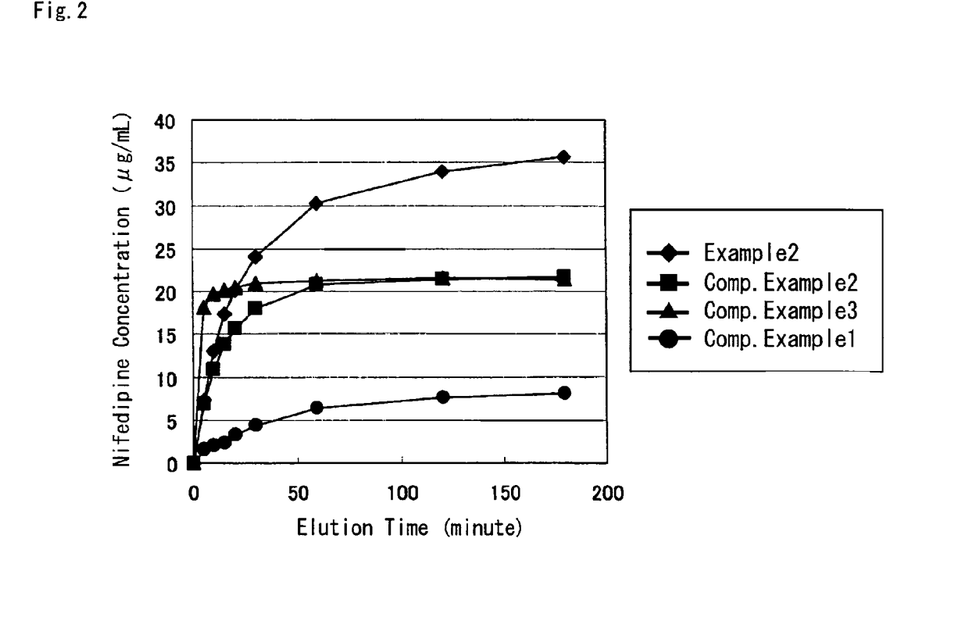
FIG. 2 is a graph showing the nifedipine concentration (μg/mL) (vertical axis) and the elution time (minute) (horizontal axis) in Test Example 2.

The elutabilities of the active ingredient (nifedipine) of the powder obtained in Comparative Example 1 and the tablets formed in Example 2, and Comparative Examples 2 and 3 in water were tested in the same manner as in Experimental Example 1. Example 2 and Comparative Examples 1 to 3 all had ultrasonic irradiation energies of 1000 J at the time of molding. The results are shown in FIG. 2.

When 180 minutes passed from the initiation of the test, the test samples of Comparative Examples 2 (PVA) and 3 (PVP) exhibited nifedipine elutabilities about 2.7 times that of the test sample of Comparative Example 1 (lactose), and the test sample of Example 2 (POVA) exhibited a nifedipine elutability about 4.5 times that of the test sample of Comparative Example 1. Therefore, the test sample of Example 2 had superior bioavailability in terms of the active ingredient elution.

Experimental Example 3

Confirmation of Crystallinity of Nifedipine

It deems that the elutabilities of nifedipine obtained in Experimental Examples 1 and 2 indicate that a higher elutability would be attained by making the nifedipine amorphous. In order to confirm whether this hypothesis is correct, the melting point of nifedipine in each sample was measured with a differential scanning calorimeter (DSC). The melting peak of the crystalline nifedipine appears in the vicinity of 174° C.

Figure 3:
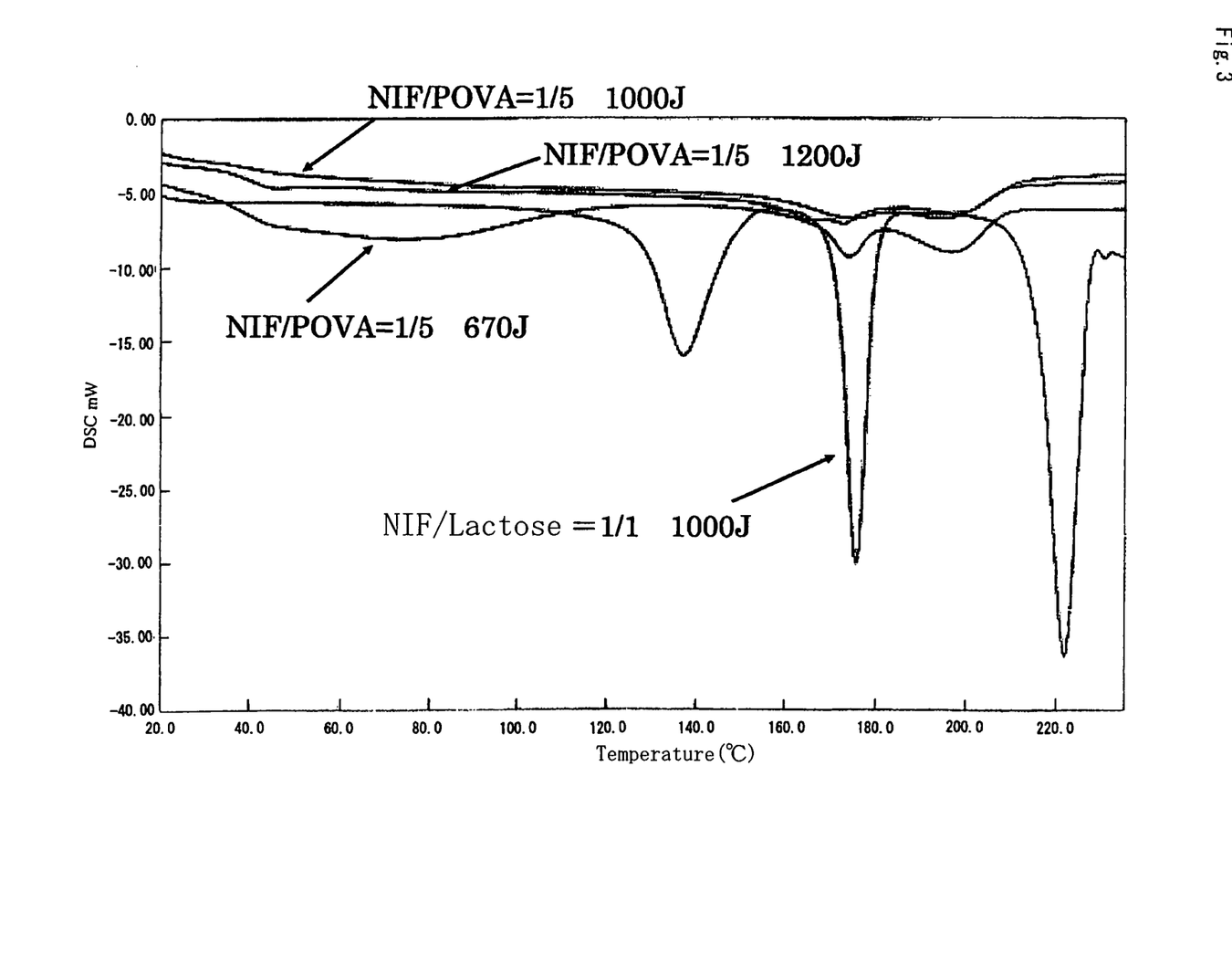

The samples (10 mg/sample) used were the powder obtained in Comparative Example 1 and the tablets formed in Examples 1 to 3. The measurement results are shown in FIG. 3.

In the sample of Example 1 (POVA; 670 J) an extremely weak peak was confirmed in the vicinity of 174° C., and in the sample of Examples 2 and 3 (POVA; 1000 J and 1200 J) no peak was confirmed in the vicinity of 174° C. Accordingly, this suggested that a large portion of the nifedipine in the sample of Example 1 was in an amorphous state, and that all of the nifedipine in the samples of Examples 2 and 3 was in an amorphous state.

In contrast, the sample of Comparative Example 1 (lactose) exhibited a melting peak in vicinity of 174° C., which is distinctive to nifedipine crystals. This indicates that the nifedipine in the sample of Comparative Example 1 was in a crystal form.

Examples 4 and 5

Ultrasonic Molding of Nifedipine Preparation With Varying Amount of Base for Solid Dispersion The nifedipine preparations were prepared by conducting ultrasonic molding in the same manner as in Example 2 (five times the weight; 1000 J) except that the amount of the base for solid dispersion used was three times the weight of nifedipine (Example 4), and seven times the weight of nifedipine (Example 5). The amount of ultrasonic irradiation energy was 1000 J.

Experimental Example 4

Elution Test 3 of Active Ingredient Nifedipine in Water

Figure 4:
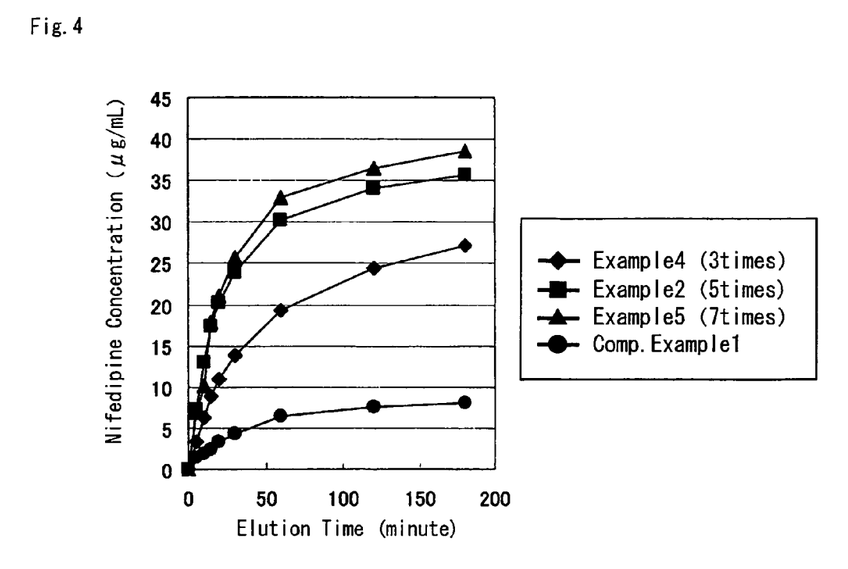
FIG. 4 is a graph showing the nifedipine concentration (μg/mL) (vertical axis) and the elution time (minute) (horizontal axis) measured in Test Example 4.

The elutabilities of the active ingredient (nifedipine) of the powder obtained in Comparative Example 1 and the tablets formed in Examples 2, 4, and 5 in water were tested in the same manner as in Experimental Example 1. Examples 2, 4, 5, and Comparative Example 1 all had ultrasonic irradiation energy of 1000 J at the time of molding. The results are shown in FIG. 4.

When 180 minutes passed from the initiation of the test, the test sample of Example 4 (containing excipients in the amount three times the weight of the active ingredient) exhibited a nifedipine elutability about 3.4 times that of the test sample of Comparative Example 1. The test sample of Example 5 exhibited a nifedipine elutability about 4.8 times that of the test sample of Comparative Example 1. This indicates that the nifedipine elution was improved by increasing the amount of POVA, which was the base for solid dispersion.

Example 6

Ultrasonic Molding of Nifedipine Preparation Using POVA

The nifedipine preparations were prepared by conducting ultrasonic molding in the same manner as in Example 2 except that a mixture of 2.5 parts by weight of HPC-SL; 1 part by weight of glycerin; 2 parts by weight of L-HPC; 1 part by weight nifedipine; and 2.5 parts by weight of POVA as the base for solid dispersion was used as the preparation material. The amount of ultrasonic irradiation energy was 1000 J.

Experimental Example 5

Elution Test 4 of Active Ingredient (Nifedipine) in Water

Figure 5:
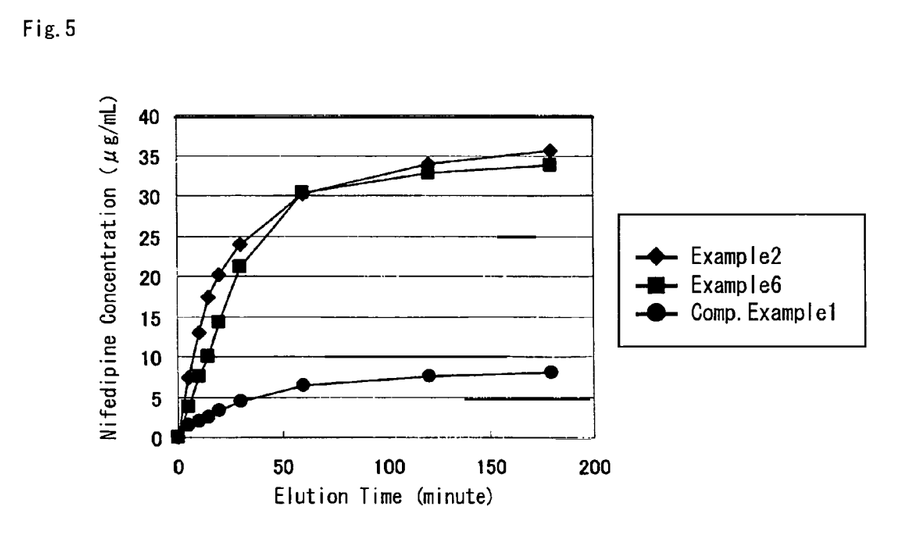
FIG. 5 is a graph showing the nifedipine concentration (μg/mL) (vertical axis) and the elution time (minute) (horizontal axis) measured in Test Example 5.

The elutabilities of the active ingredient (nifedipine) of the powder obtained in Comparative Example 1 and the tablets formed in Example 2 and Example 6 in water were tested. The results are shown in FIG. 5.

When 180 minutes passed from the initiation of the test, the test sample of Example 6 (containing excipients in the amount 2.5 times the weight of the active ingredient and additional additives) exhibited a nifedipine elutability about 4.2 times that of the test sample of Comparative Example 1.

Examples 7 to 9

Preparation of Base for Solid Dispersion by Melt Extrusion Using POVA

The base for solid dispersion was prepared using Melt Indexer P101 (manufactured by Toyo Seiki Co., Ltd.)

First, 8 g of Pova and 2 g of glycerin were mixed, and 2 g of nifedipine was then added and well-mixed, obtaining a sample powder. Three grams of this sample powder was weighed and placed in a cylinder (9 mm in diameter) provided in the device. The cylinder had been heated to 160° C. By applying pressure (2160 g) to a piston on the upper portion of the cylinder, the melted sample was extruded from an orifice (2 mm in diameter) in a bottom portion of the cylinder, and cord shaped base for solid dispersion was prepared by melt extrusion molding. (Example 7)

The base for solid dispersion was prepared by melt extrusion molding in the same manner except that the temperature of the cylinder was changed to 170° C. (Example 8).

The base for solid dispersion was attempted to be prepared in the same manner except that the temperature of the cylinder was changed to 190° C. (Example 9); however, because the pressure of 2160 g was too high, the application pressure was changed to 1325 g and the extrusion molding was conducted to prepare the base for solid dispersion.

Experimental Example 6

Elution Test 5 of Active Ingredient (Nifedipine) in Water

Figure 6:
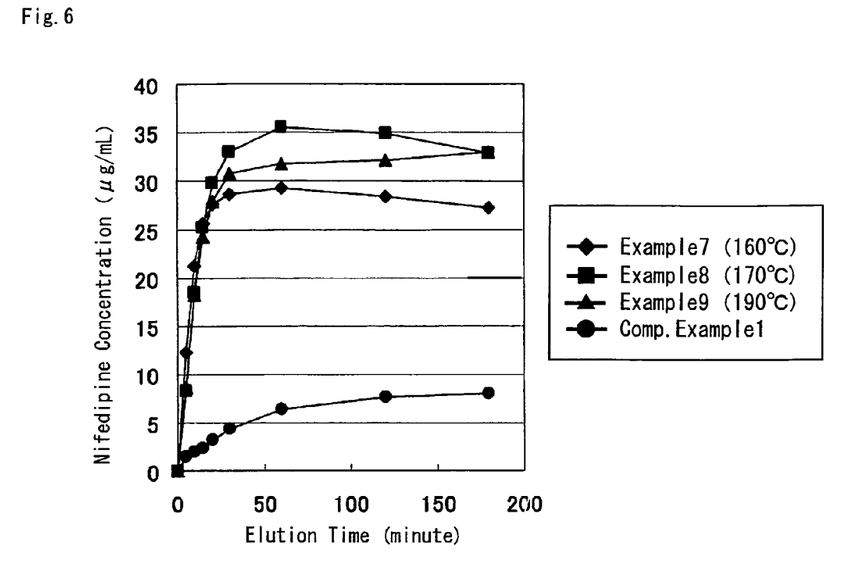
FIG. 6 is a graph showing the nifedipine concentration (μg/mL) (vertical axis) and the elution time (minute) (horizontal axis) measured in Test Example 6.

The elutabilities of the active ingredient (nifedipine) of the powder obtained in Comparative Example 1 and the bases for solid dispersion formed in Examples 7 to 9 in water were tested in the same manner as in Experimental Example 1. The results are shown in FIG. 6.

When 180 minutes passed from the initiation of the test, the test sample of Example 7 (160° C.) exhibited a nifedipine elutability about 3.4 times that of the test sample of Comparative Example 1. The test samples of Example 8 (170° C.) and Example 9 (190° C.) both exhibited a nifedipine elutability about 4.1 times that of the test sample of Comparative Example 1. This indicates that the base for solid dispersion of the present invention produced by melt extrusion molding also exhibits excellent nifedipine elutability.

Comparative Example 5

Preparation of Base for Solid Dispersion by Melt Extrusion Using PVA

The base for solid dispersion was prepared by melt extrusion in the same manner as in Example 8 (170° C.) except that PVA was used instead of POVA.

Comparative Example 6

Preparation of Base for Solid Dispersion by Melt Extrusion Using PVP

The base for solid dispersion was prepared by melt extrusion in the same manner as in Example 8 (170° C.) except that PVP was used instead of POVA.

Experimental Example 7

Elution Test 6 of Active Ingredient (Nifedipine) in Water

Figure 7:
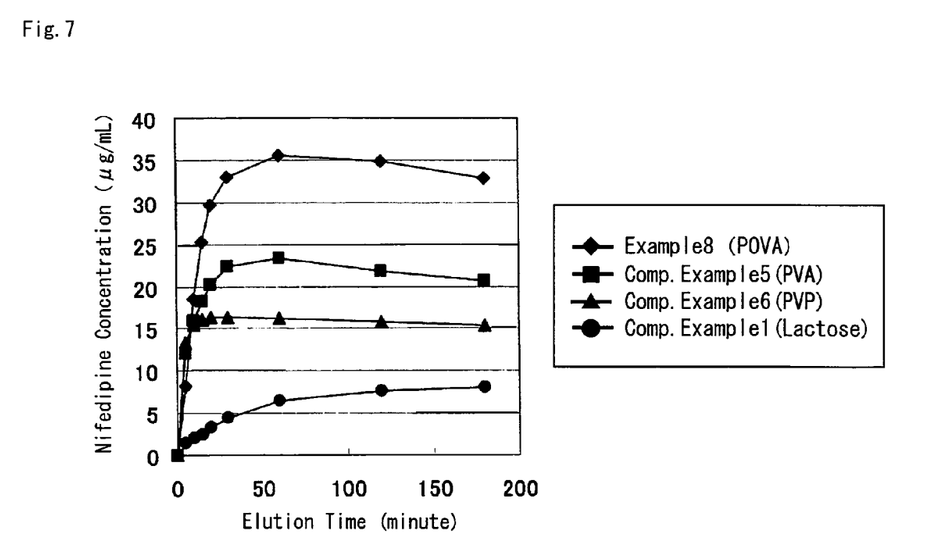
FIG. 7 is a graph showing the nifedipine concentration (μg/mL) (vertical axis) and the elution time (minute) (horizontal axis) measured in Test Example 7.

The elutabilities of the active ingredient (nifedipine) of the powder obtained in Comparative Example 1 and the bases for solid dispersion formed in Example 8, and Comparative Examples 5 and 6 in water were tested in the same manner as in Experimental Example 1. The results are shown in FIG. 7.

When 180 minutes passed from the initiation of the test, the test sample of Example 8 (170° C.) exhibited a nifedipine elutability about 4.1 times that of the test sample of Comparative Example 1. In contrast, the test sample of Comparative Example 5 (PVA, 170° C.), and the test sample of Comparative Example 6 (PVP, 170° C.) respectively exhibited nifedipine elutability merely about 2.6 times and about 1.9 times that of the test sample of Comparative Example 1.

INDUSTRIAL APPLICABILITY

The present invention can be applied to a technique relating to make poorly soluble components amorphous to improve its solubility.

The invention claimed is:

1. A solid dispersion comprising a poorly soluble component and a polyvinyl alcohol-based copolymer obtained by copolymerizing at least one member selected from the group consisting of polyvinyl alcohols and derivatives thereof with at least one polymerizable vinyl monomer selected from the group consisting of compounds represented by General Formula [1]:

$$H_2C=C(R^1)-COOR^2 \qquad [1]$$

wherein $R^1$ represents a hydrogen atom or a methyl group, and $R^2$ represents a hydrogen atom or a $C_{1-4}$ alkyl group; wherein the poorly soluble component is a poorly soluble medicament that has a solubility in water at 25° C. of less than 10 mg/mL;

a part or all of the poorly soluble component being contained in an amorphous state;

the polyvinyl alcohol-based copolymer being used as a base for solid dispersion; and the weight of the polyvinyl alcohol-based copolymer is 1 to 20 times the weight of the poorly soluble component.

2. A medical composition comprising the solid dispersion defined in claim 1.

3. The solid dispersion according to claim 1, which is formed by heating a mixture of a poorly soluble component and a polyvinyl alcohol-based copolymer obtained by copolymerizing at least one member selected from the group consisting of polyvinyl alcohols and derivatives thereof with at least one polymerizable vinyl monomer selected from the group consisting of compounds represented by General Formula [1]:

$$H_2C=C(R^1)-COOR^2 \qquad [1]$$

wherein $R^1$ represents a hydrogen atom or a methyl group, and $R^2$ represents a hydrogen atom or a $C_{1-4}$ alkyl group.

4. A medical composition comprising the solid dispersion defined in claim 3.

5. The solid dispersion according to claim 3, wherein the heating is conducted by one means selected from supersonic treatment, biaxial kneading treatment, melting treatment, uniaxial and biaxial melt-extruding treatment, microwave treatment, and thermal mechanochemical treatment, or a combination thereof.

6. A medical composition comprising the solid dispersion defined in claim 5.

7. A method for producing a solid dispersion comprising the step of:

heating a mixture of a poorly soluble component and a polyvinyl alcohol-based copolymer obtained by copolymerizing at least one member selected from the group consisting of polyvinyl alcohols and derivatives thereof with at least one polymerizable vinyl monomer selected from the group consisting of compounds represented by General Formula [1]:

$$H_2C=C(R^1)-COOR^2 \qquad [1]$$

wherein $R^1$ represents a hydrogen atom or a methyl group, and $R^2$ represents a hydrogen atom or a $C_{1-4}$ alkyl group;

wherein the poorly soluble is being a poorly soluble medicament that has a solubility in water at 25° C. of less than 10 mg/mL;

a part or all of the poorly soluble component being contained in an amorphous state;

the polyvinyl alcohol-based copolymer being used as a base for solid dispersion; and the weight of the polyvinyl alcohol-based copolymer is 1 to 20 times the weight of the poorly soluble component.

* * * * *